(12) United States Patent
Ryu et al.

(10) Patent No.: US 10,487,074 B2
(45) Date of Patent: Nov. 26, 2019

(54) METHOD FOR PURIFYING BENZOPYRAN DERIVATIVE, CRYSTAL FORM THEREOF, AND METHOD FOR PREPARING CRYSTAL FORM

(71) Applicant: HANLIM PHARMACEUTICAL CO., LTD., Yongin-si, Gyeonggi-do (KR)

(72) Inventors: Jae-Chun Ryu, Yongin-si (KR); Yong-Kyun Park, Seongnam-si (KR); Hyun-Kyu Kim, Gwangmyeong-si (KR); Dong-Yeop Shin, Gunpo-si (KR)

(73) Assignee: HANLIM PHARMACEUTICAL CO., LTD., Yongin-si, Gyeonggi-do (KR)

( * ) Notice: Subject to any disclaimer, the term of this patent is extended or adjusted under 35 U.S.C. 154(b) by 0 days.

(21) Appl. No.: 15/779,236

(22) PCT Filed: Nov. 24, 2016

(86) PCT No.: PCT/KR2016/013585
§ 371 (c)(1),
(2) Date: May 25, 2018

(87) PCT Pub. No.: WO2017/090991
PCT Pub. Date: Jun. 1, 2017

(65) Prior Publication Data
US 2019/0248768 A1    Aug. 15, 2019

(30) Foreign Application Priority Data

Nov. 27, 2015  (KR) .......................... 10-2015-0167238

(51) Int. Cl.
*C07D 405/12*    (2006.01)
(52) U.S. Cl.
CPC ........ *C07D 405/12* (2013.01); *C07B 2200/13* (2013.01)

(58) Field of Classification Search
CPC combination set(s) only.
See application file for complete search history.

(56) References Cited

U.S. PATENT DOCUMENTS

2014/0018402 A1* 1/2014 Yi ..................... A61K 31/4178
514/397

FOREIGN PATENT DOCUMENTS

| KR | 10-2004-0014023 A | 2/2004 | |
| KR | 10-2011-0038011 A | 4/2011 | |
| KR | 10-1045616 B1 | 7/2011 | |
| KR | 10-2012-0112162 A | 10/2012 | |
| KR | 20120112162 A | * 10/2012 | ........... A61K 9/0048 |
| KR | 10-2014-0146719 A | 12/2014 | |
| WO | 2010/000469 A2 | 1/2010 | |

* cited by examiner

*Primary Examiner* — Amanda L Aguirre
(74) *Attorney, Agent, or Firm* — Vorys, Sater, Seymour & Pease LLP; Mih Suhn Koh

(57) ABSTRACT

The present invention provides a process for purifying (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran, comprising converting an amorphous (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran to a crystalline form thereof. And also, the present invention provides a novel crystalline form of (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran and processes for preparing the same.

23 Claims, 8 Drawing Sheets

METHOD FOR PURIFYING BENZOPYRAN DERIVATIVE, CRYSTAL FORM THEREOF, AND METHOD FOR PREPARING CRYSTAL FORM

TECHNICAL FIELD

The present invention relates to a process for purifying a crude benzopyran derivative. More specifically, the present invention relates to a process for purifying a benzopyran derivative, comprising converting an amorphous crude benzopyran derivative to a crystalline form thereof. And also, the present invention relates to a novel crystalline form of the benzopyran derivative and processes for preparing the same.

BACKGROUND ART

The benzopyran derivative of Formula 1, whose chemical name is (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran, is known as a compound having therapeutic effects for cancer, rheumatoid arthritis, etc. (Korean Patent No. 10-0492252). And also, the compound of Formula 1 can be prepared as an eye drop formulation based on a low-molecular weight material; and usefully applied to the prevention and treatment of macular degeneration, without injecting directly into the affected site as in the antibody injection therapy (Korean Patent Publication No. 10-2012-0112162).

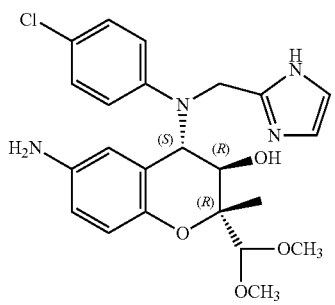

<Formula 1>

A process for preparing the compound of Formula 1 has been disclosed in Korean Patent No. 10-0492252. Specifically, as shown in the following reaction scheme 1, the process for preparing the compound of Formula 1 comprises converting the olefin compound of Formula 4a to the epoxide compound of Formula 3a; reacting the epoxide compound of Formula 3a with (4-chlorophenyl)(1H-imidazol-2-ylmethyl)amine to obtain the compound of Formula 2a; and reducing the compound of Formula 2a to obtain the compound of Formula 1.

<Reaction Scheme 1>

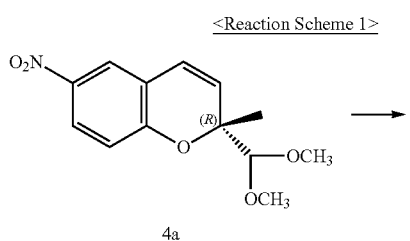

4a

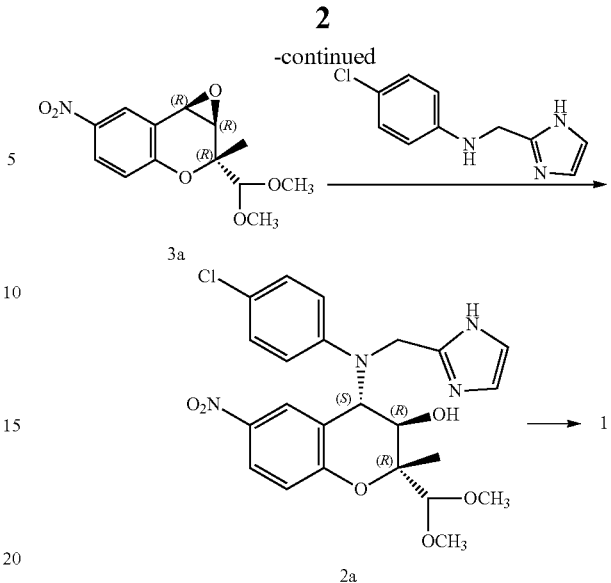

The compound of Formula 1 obtained in said process is isolated by filtering the reaction mixture obtained from the reduction to remove a solid, concentrating the filtrate, and then purifying the resulting residue with a silica gel column chromatography.

The present inventors have found that, as a result of performing the analyses on the compound of Formula 1 prepared according to the method disclosed in Korean Patent No. 10-0492252, the obtained product has low purity (less than 97 wt/wt % as an anhydrous form) and high water contents (more than 1 wt/wt %). Especially, the compound of Formula 1 prepared according to the method disclosed in Korean Patent No. 10-0492252 includes residual impurities (for example, organic impurities, inorganic impurities, residual solvents, etc.) originated from the preparation or rapidly-decomposed degradation products, and thus the purity thereof is not within a suitable range (for example, 99.0% or more) according to the Regulation on Drug Product Authorization of the Ministry of Food and Drug Safety, which causes the problem that it cannot be directly used as an active pharmaceutical ingredient. And also, the compound of Formula 1 prepared according to the method disclosed in Korean Patent No. 10-0492252 shows very high hygroscopicity. For example, the water contents thereof are increased to 2.30 wt/wt % in 1 day under the accelerated condition; and thus strict control thereof is required. In addition, the product itself obtained immediately after the preparation has also high water contents, which is not suitable for use as an active pharmaceutical ingredient.

DISCLOSURE

Technical Problem

The present inventors carried out various researches in order to develop a process capable of fundamentally solving the problems of low purity and high water contents (as well as high hygroscopicity) of the benzopyran derivative (i.e., the crude compound of Formula 1) prepared according to the prior art method. Surprisingly, it has been found that the product prepared according to the prior art method (Korean Patent No. 10-0492252) is obtained in an amorphous form. And also, it has been found that, when the amorphous product is converted to a crystalline form (e.g., a crystalline form A having a specific XRPD pattern, a specific DSC thermogram, or a specific TGA thermogram), the purity of the product can be remarkably increased and the residual water contents of the resulting crystalline form can be remarkably reduced to 0.2 wt/wt % or less. In addition, it has been found that the resulting crystalline form does not show hygroscopicity substantially, which can fundamentally solve the problems of the amorphous form having hygroscopicity.

Therefore, it is an object of the present invention to provide a process for purifying the compound of Formula 1, comprising converting a crude benzopyran derivative (i.e., the compound of Formula 1) to a crystalline form thereof.

And also, it is another object of the present invention to provide a crystalline form of the compound of Formula 1.

And also, it is still another object of the present invention to provide processes for preparing the crystalline form of the compound of Formula 1.

Technical Solution

In accordance with an aspect of the present invention, there is provided a process for purifying a compound of Formula 1, comprising converting a crude compound of Formula 1 to a crystalline form thereof.

<Formula 1>

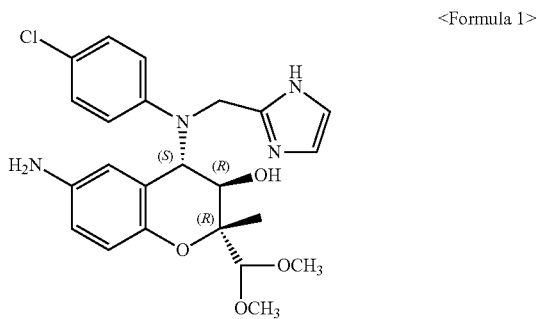

In accordance with another aspect of the present invention, there is provided a crystalline form of the compound of Formula 1. In an embodiment, the crystalline form of the compound of Formula 1 may be a crystalline form A having an XRPD pattern with peaks at 12.27, 12.65, 16.07, 19.06 and 26.48°2θ±0.2°2θ.

In accordance with still another aspect of the present invention, there is provided a process for preparing a crystalline form of the compound of Formula 1, comprising dissolving an amorphous compound of Formula 1 in an organic solvent to obtain a solution; stirring, distilling, or cooling the solution to form a solid or distilling and then cooling the solution to form a solid; and isolating the solid.

In accordance with still another aspect of the present invention, there is provided a process for preparing a crystalline form of the compound of Formula 1, comprising dissolving an amorphous compound of Formula 1 in an organic solvent to obtain a solution; adding the solution to an antisolvent to form a solid or adding an antisolvent to the solution to form a solid; and isolating the solid.

In accordance with still another aspect of the present invention, there is provided a process for preparing a crystalline form of the compound of Formula 1, comprising dissolving an amorphous compound of Formula 1 in water by adding an acid thereto to obtain a solution; adding a base to the solution to form a solid; and isolating the solid.

Advantageous Effects

It has been found by the present invention that the compound of Formula 1 obtained by the prior art method (i.e., the method disclosed in Korean Patent No. 10-0492252) is obtained in an amorphous form having low purity and high water contents (as well as high hygroscopicity). The purification process according to the present invention can provide the compound of Formula 1 in a crystalline form having high purity and reduced water contents. The purification process has an advantage that it can be easily applied for industrial mass production. And also, the crystalline form (e.g., the crystalline form A of the compound of Formula 1), which has a specific XRPD pattern, a specific DSC thermogram, or a specific TGA thermogram, has superior initial properties (i.e., having high purity and reduced water contents). Especially, the crystalline form A of the compound of Formula 1 does not show hygroscopicity substantially; and can be maintained in a stable form, without showing any change in the crystallinity, even under heated and accelerated conditions. Therefore, the crystalline form A of the compound of Formula 1 has properties suitable for formulating into therapeutic dosage forms; and thus has advantages in allowing efficient formulation without loss of the active pharmaceutical ingredient and in long-term storage thereof.

BEST MODE

Figure 1:
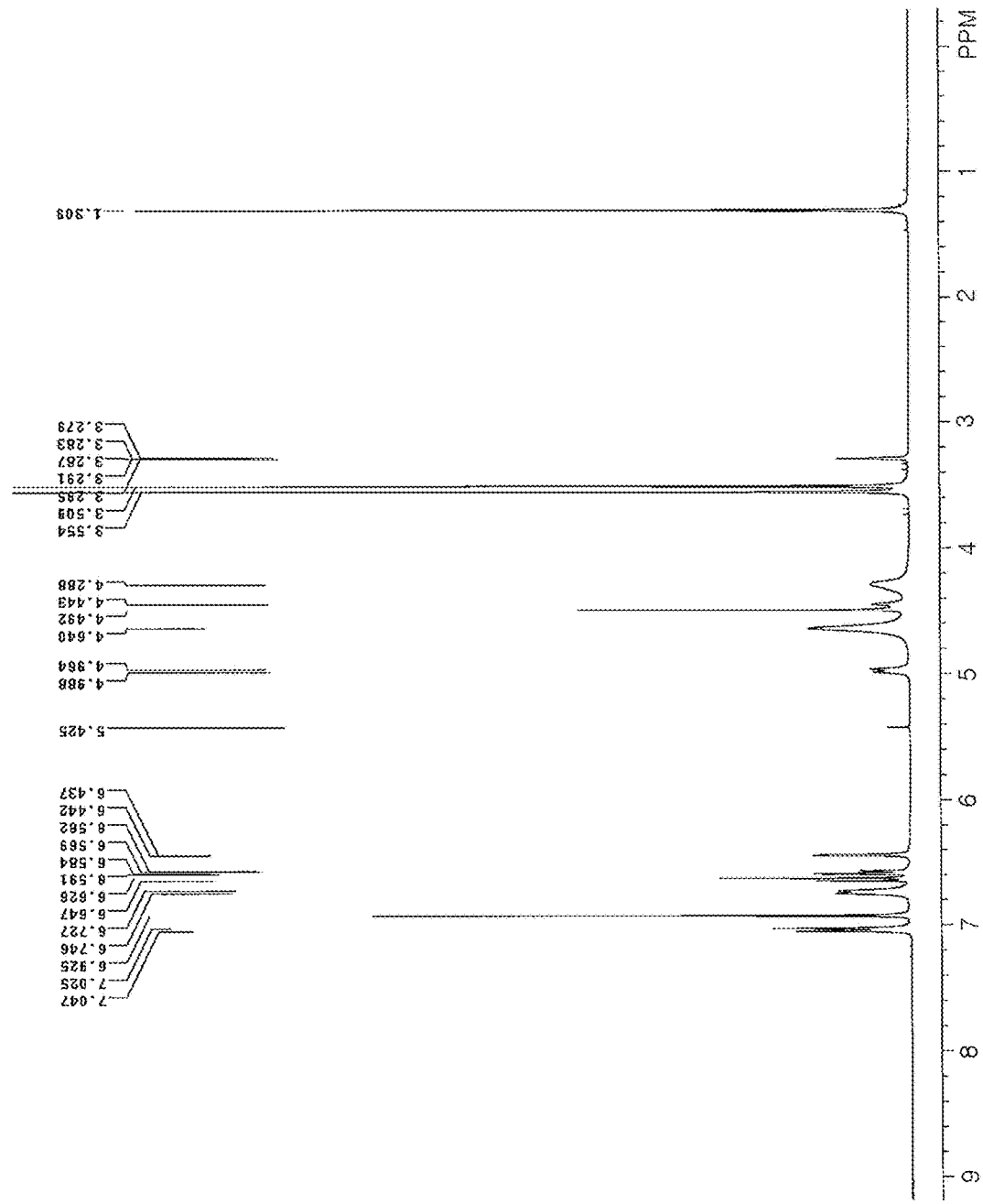
FIGS. 1 to 4 show the $^1$H-NMR spectrum (FIG. 1), the XRPD spectrum (FIG. 2), the DSC thermogram (FIG. 3), and the TGA thermogram (FIG. 4) of the benzopyran derivative (i.e., the compound of Formula 1) prepared according to the method disclosed in Korean Patent No. 10-0492252, respectively.

The present invention provides a process for purifying a compound of Formula 1, comprising converting a crude compound of Formula 1 to a crystalline form thereof.

<Formula 1>

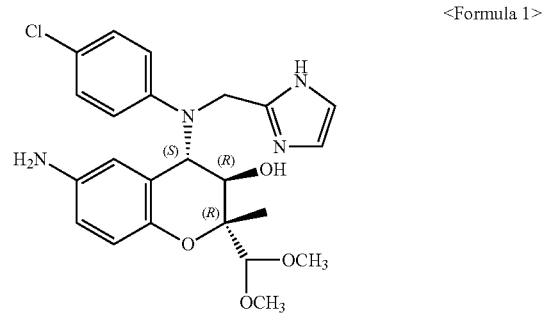

As used herein, the term 'crude compound of Formula 1' refers to the compound in which the contents of the compound of Formula 1 are 97 wt/wt % or less, preferably less than 98 wt/wt %, as an anhydrous form thereof. For example, the crude compound of Formula 1 may be the compound obtained by the method disclosed in Korean Patent No. 10-0492252. In an embodiment, the crude compound of Formula 1 may be the amorphous compound of Formula 1 obtained by the method disclosed in Korean Patent No. 10-0492252.

It has been found by the present invention that the compound of Formula 1 obtained by the prior art method (i.e., the method disclosed in Korean Patent No. 10-0492252) is obtained in an amorphous form having low purity and high water contents (as well as high hygroscopicity). The purification process according to the present invention can provide the compound of Formula 1 in a crystalline form having high purity and reduced water contents. The purification process has an advantage that it can be easily applied for industrial mass production. As used herein, the term 'a compound of Formula 1 having high purity' refers to the compound of Formula 1 in which the contents of the compound of Formula 1 are 98 wt/wt % or more, preferably 99 wt/wt % or more, as an anhydrous form thereof. And also, the term 'a compound of Formula 1 having reduced water contents' refers to the compound of Formula 1 in which the water contents are 0.5 wt/wt % or less, preferably 0.3 wt/wt % or less, more preferably 0.2 wt/wt % or less.

In the purification process of the present invention, the crystalline form may be a crystalline form A; and the crystalline form A may have an X-Ray Powder Diffraction (XRPD) pattern with characteristic peaks at 12.27, 12.65, 16.07, 19.06 and 26.48°2θ±0.2°2θ. Preferably, the crystalline form A of the compound of Formula 1 may have an XRPD pattern with peaks at 12.27, 12.65, 16.07, 16.48, 17.89, 18.89, 19.06, 19.31 and 26.48°2θ±0.2°2θ. More preferably, the crystalline form A of the compound of Formula 1 may have an XRPD pattern shown in FIG. 6.

Figure 7:
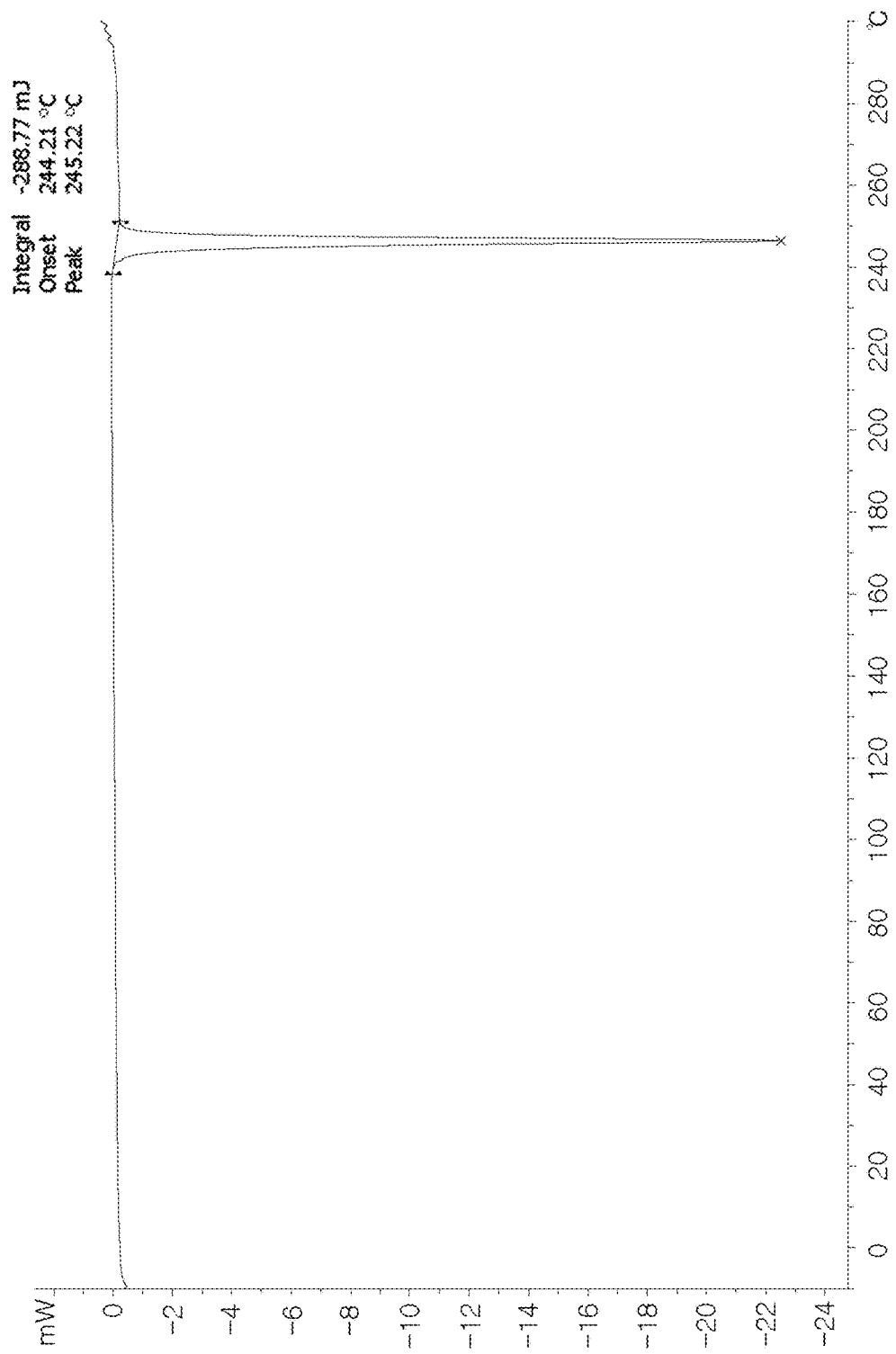

And also, the crystalline form A of the compound of Formula 1 may have a differential scanning calorimetry (DSC) thermogram showing an endothermic peak at between 240° C. and 250° C., for example the DSC thermogram shown in FIG. 7.

Figure 8:
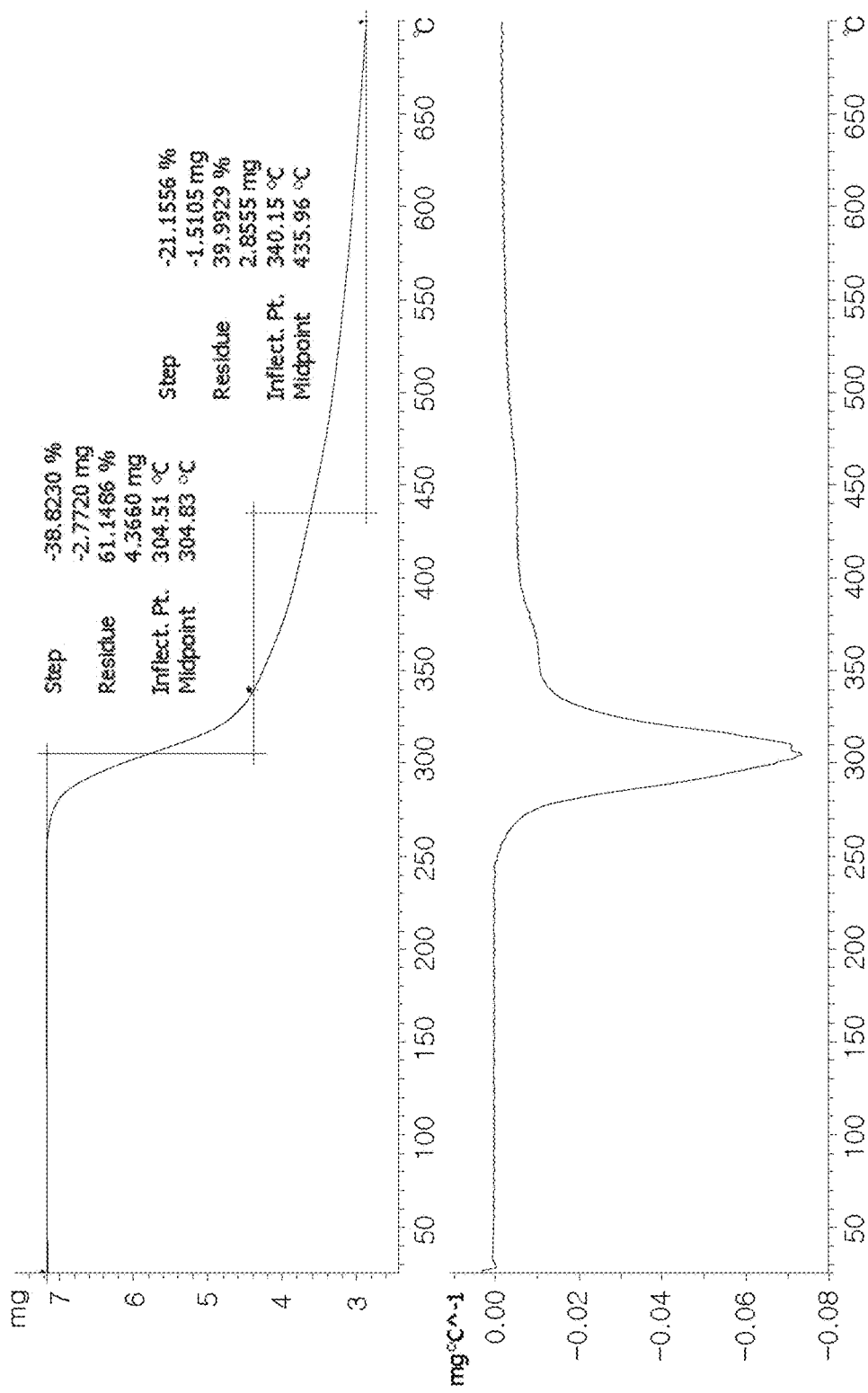

And also, the crystalline form A of the compound of Formula 1 may have a thermogravimetric analysis (TGA) thermogram showing a weight loss at between 300° C. and 310° C., for example the TGA thermogram shown in FIG. 8.

The present invention provides a crystalline form of the compound of Formula 1.

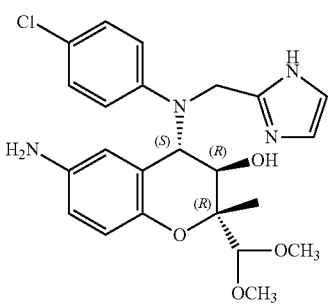

<Formula 1>

The crystalline form A of the compound of Formula 1 has superior initial properties (i.e., having high purity and reduced water contents). Especially, the crystalline form A of the compound of Formula 1 does not show hygroscopicity substantially; and can be maintained in a stable form, without showing any change in the crystallinity, even under heated and accelerated conditions. Therefore, the crystalline form A of the compound of Formula 1 has properties suitable for formulating into therapeutic dosage forms; and thus has advantages in allowing efficient formulation without loss of the active pharmaceutical ingredient and in long-term storage thereof.

As used herein, 'the compound which does not show hygroscopicity substantially' refers to the compound showing 0.05 wt/wt % or less, preferably 0.03 wt/wt % or less, more preferably 0.02 wt/wt % or less of the water content change, when stored under the accelerated condition (40° C., 75% RH) for 2 weeks (Δ water contents=the water contents when stored for 2 weeks–the initial water contents); or the compound showing 0.05 wt/wt % or less of the water content change, when stored under the heated condition (100° C.) for 2 weeks (Δ water contents=the water contents when stored for 2 weeks–the initial water contents); or the compound showing 0.3 wt/wt % or less, preferably 0.2 wt/wt % or less of the water content change, when stored under the humid condition (25° C., 98% RH) for 2 weeks (Δ water contents=the water contents when stored for 2 weeks–the initial water contents).

The crystalline form of the compound of Formula 1 may be a crystalline form A; and the crystalline form A may have an XRPD pattern with peaks at 12.27, 12.65, 16.07, 19.06 and 26.48°2θ±0.2°2θ. Preferably, the crystalline form of the compound of Formula 1 may have an XRPD pattern with peaks at 12.27, 12.65, 16.07, 16.48, 17.89, 18.89, 19.06, 19.31 and 26.48°2θ±0.2°2θ. More preferably, the crystalline form A of the compound of Formula 1 may have an XRPD pattern shown in FIG. 6.

And also, the crystalline form A of the compound of Formula 1 may have a differential scanning calorimetry (DSC) thermogram showing an endothermic peak at between 240° C. and 250° C., for example the DSC thermogram shown in FIG. 7.

And also, the crystalline form A of the compound of Formula 1 may have a thermogravimetric analysis (TGA) thermogram showing a weight loss at between 300° C. and 310° C., for example the TGA thermogram shown in FIG. 8.

The present invention provides a process for preparing a crystalline form of the compound of Formula 1, which can be easily applied for industrial mass production.

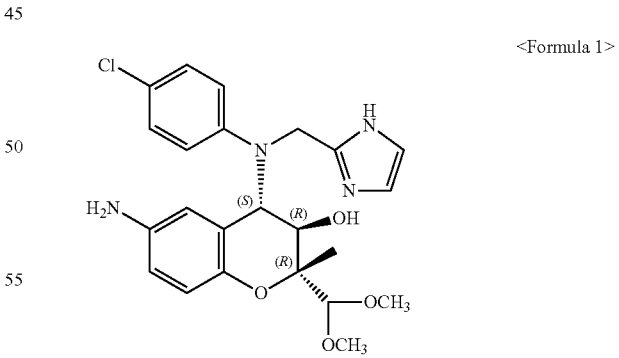

<Formula 1>

The process for preparing a crystalline form of the compound of Formula 1 of the present invention uses the amorphous compound of Formula 1 as a starting material, which may be prepared according to the method disclosed in Korean Patent No. 10-0492252.

In an embodiment, the present invention provides a process for preparing a crystalline form of the compound of Formula 1, comprising dissolving an amorphous compound of Formula 1 in an organic solvent to obtain a solution; stirring, distilling, or to cooling the solution to form a solid or distilling and then cooling the solution to form a solid; and isolating the solid (that is, a process through recrystallization). The organic solvent may be any solvent that can dissolve the amorphous compound of Formula 1 and one organic solvent or a combination of two or more organic solvents may be used. For example, the organic solvent may be one or more selected from the group consisting of methanol, ethanol, isopropanol, acetone, methyl ethyl ketone, acetonitrile, ethyl acetate, dichloromethane, tetrahydrofuran, dimethyl sulfoxide, dimethylformamide, and N-methyl-2-pyrrolidone. Preferably, the organic solvent may be one or more selected from the group consisting of methanol, ethanol, isopropanol, acetone, acetonitrile, dichloromethane, ethyl acetate, and methyl ethyl ketone. The dissolving may be carried out at the temperature ranging from room temperature to reflux temperature of the used solvent(s). The forming a solid may be performed by stirring, distilling, or cooling the solution; or by distilling the solution to reduce the volume of solvent, followed by cooling the resulting solution. The isolating the solid (i.e., the crystalline form) may be performed by conventional filtering (e.g., filtering under reduced pressure), drying (e.g., drying at about 50° C.), and so on.

In another embodiment, the present invention provides a process for preparing a crystalline form of the compound of Formula 1, comprising dissolving an amorphous compound of Formula 1 in an organic solvent to obtain a solution; adding the solution to an antisolvent to form a solid or adding an antisolvent to the solution to form a solid; and isolating the solid (that is, a process using solvent/antisolvent). The organic solvent may be any solvent that can dissolve the amorphous compound of Formula 1 and one organic solvent or a combination of two or more organic solvents may be used. For example, the organic solvent may be one or more selected from the group consisting of methanol, ethanol, isopropanol, acetone, methyl ethyl ketone, acetonitrile, ethyl acetate, dichloromethane, tetrahydrofuran, dimethyl sulfoxide, dimethylformamide, and N-methyl-2-pyrrolidone. The dissolving may be carried out at the temperature ranging from room temperature to reflux temperature of the used solvent(s). The antisolvent may be one or more selected from the group consisting of water, hexane, heptane, diethyl ether, isopropyl ether, di-n-butyl ether, and toluene, but not limited thereto. The isolating the solid (i.e., the crystalline form) may be performed by conventional filtering (e.g., filtering under reduced pressure), drying (e.g., drying at about 50° C.), and so on.

In still another embodiment, the present invention provides a process for preparing a crystalline form of the compound of Formula 1, comprising dissolving an amorphous compound of Formula 1 in water by adding an acid thereto to obtain a solution; adding a base to the solution to form a solid; and isolating the solid (that is, a process through crystallization by pH control). The acid may be any acid that can provide an acidic pH. For example, the acid may be one or more selected from the group consisting of hydrochloric acid, acetic acid, and formic acid, but not limited thereto. And also, the base may be any base that can neutralize the used acid to form a solid. For example, the base may be one or more selected from the group consisting of sodium hydroxide, potassium hydroxide, sodium bicarbonate, and sodium carbonate, but not limited thereto. The acid and/or base may be used typically in the form of an aqueous solution.

The crystalline form obtained by said processes for preparing a crystalline form of the compound of Formula 1 of the present invention is obtained in a crystalline form A. The crystalline form A may have an XRPD pattern with characteristic peaks at 12.27, 12.65, 16.07, 19.06 and 26.48°2θ±0.2°2θ. Preferably, the crystalline form A of the compound of Formula 1 may have an XRPD pattern with peaks at 12.27, 12.65, 16.07, 16.48, 17.89, 18.89, 19.06, 19.31 and 26.48°2θ±0.2°2θ. More preferably, the crystalline form A of the compound of Formula 1 may have an XRPD pattern shown in FIG. 6. And also, the crystalline form A of the compound of Formula 1 may have a differential scanning calorimetry (DSC) thermogram showing an endothermic peak at between 240° C. and 250° C., for example the DSC thermogram shown in FIG. 7. And also, the crystalline form A of the compound of Formula 1 may have a thermogravimetric analysis (TGA) thermogram showing a weight loss at between 300° C. and 310° C., for example the TGA thermogram shown in FIG. 8.

The present invention will be described in further detail with reference to the following examples and experimental examples. These examples and experimental examples are for illustrative purposes only and are not intended to limit the scope of the present invention.

In the following examples and experimental examples, the high performance liquid chromatography (HPLC) analyses were carried out under the following conditions:

Analytical column: C18, 4.6×250 mm, 5 μm
Mobile phase: buffer solution/acetonitrile=40/60 (v/v)
Buffer solution: ammonium formate (0.657 g) was taken and then added to a 1 L volumetric flask. Water was added thereto to the mark so as to dissolve ammonium formate and then the pH of the resulting solution was adjusted to pH 5.5±0.2 with a diluted formic acid.
Wavelength: 254 nm
Column temperature: 30° C.
Flow rate: 1.0 mL/min.
Injection volume: 10 μL The X-ray powder diffraction (XRPD) analyses were carried out with the PANalytical's X-pert Pro X-ray powder diffractometer. The measurements at the angles ranging from 3 to 80°2θ values were performed at a scanning rate of 3° per second, using CuK$_{\alpha 1}$ radiation ($\lambda_{\alpha 1}$=1.54060 Å) produced at the conditions of 40 mA and 40 kV.

The differential scanning calorimetry (DSC) analyses were carried out with the Mettler Toledo's DSC 823e Differential Scanning calorimeter, under the following conditions: start temperature 10° C., end temperature 300° C., heating rate 10° C./min, and purged nitrogen gas flow rate 50 mL/min.

The thermogravimetric analyses (TGA) were carried out with the Mettler Toledo's TGA/SDTA 851 Thermogravimetric Analyzer, under the following conditions: start temperature 25° C., end temperature 700° C., and heating rate 10° C./min.

Preparation Example: (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran (Compound of Formula 1)

According to the known method (Example 23 of Korean Patent No. 10-0492252), the nitro compound (52.10 g, 106.56 mmol) was dissolved in methanol (300 mL); and then 10% Pd/C (5.0 g) was added thereto. The mixture was hydrogenated under 3 atmosphere pressure of $H_2$ for 12 hours. The reaction mixture was filtered through a Celite pad to remove a solid; and the filtrate was concentrated. The resulting residue was purified with silica gel column chromatography (methanol:dichloromethane=5:95 (v/v)) to give the title compound 36.52 g (Yield: 75%). The melting point, the purity (the contents of the compound of Formula 1 (as an anhydrous form) in the product), the water contents, and the $^1$H-NMR spectrum (FIG. 1) of the resulting product are as follows:

Melting point: 191-195° C.

Purity: 96.96 wt/wt %

Water contents: 1.05 wt/wt %

$^1$H-NMR (400 MHz, CD$_3$OD) δ (ppm): 1.309 (s, 3H), 3.509 (s, 3H), 3.554 (s, 3H), 4.288 (m, 2H), 4.443-4.492 (d, 2H), 4.964-4.988 (d, 1H), 6.437-6.442 (d, 1H), 6.562-6.591 (m, 1H), 6.626-6.647 (d, 1H), 6.727-6.746 (d, 2H), 6.925 (s, 2H), 7.025-7.047 (d, 2H).

Figure 2:
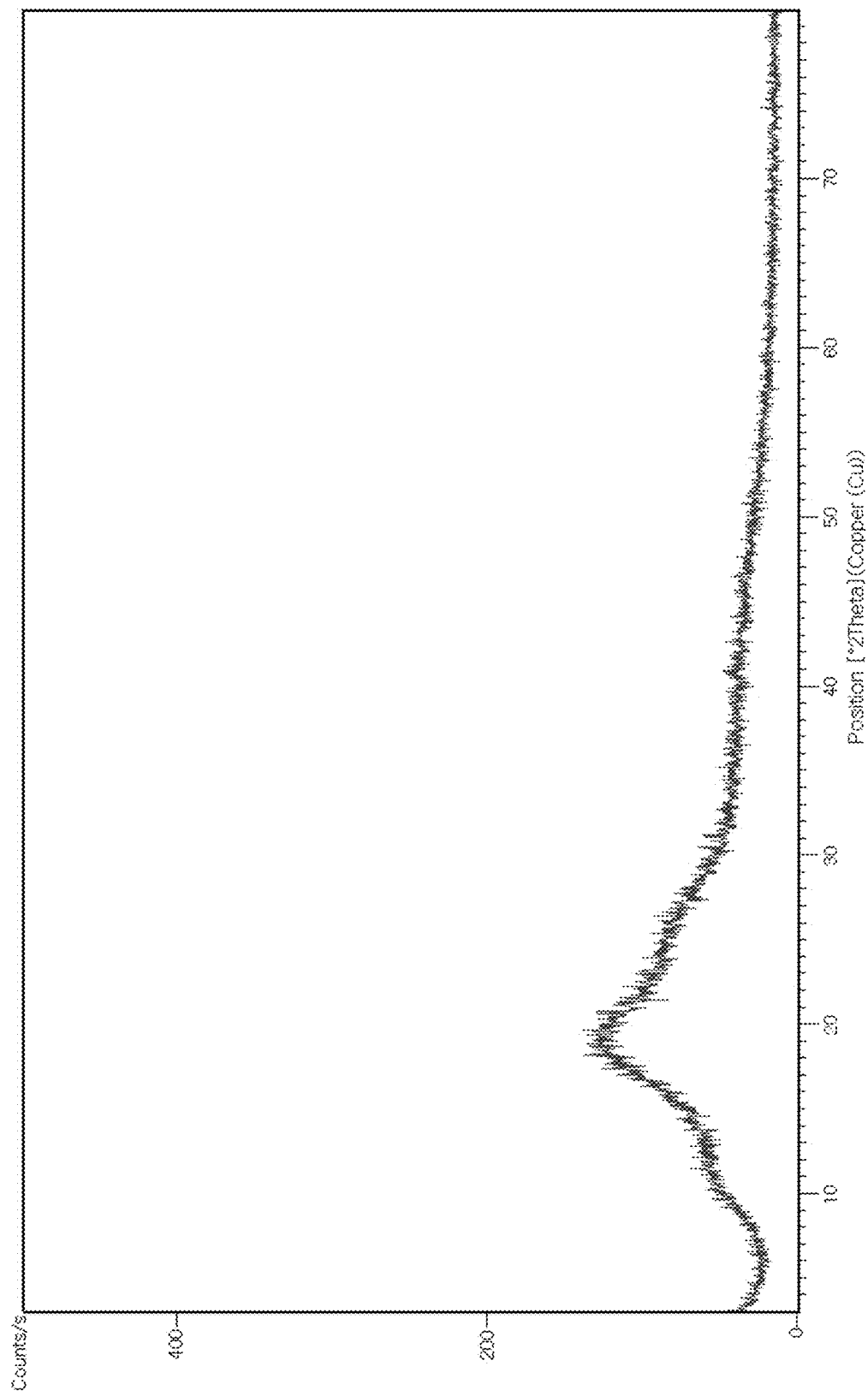
Figure 3:
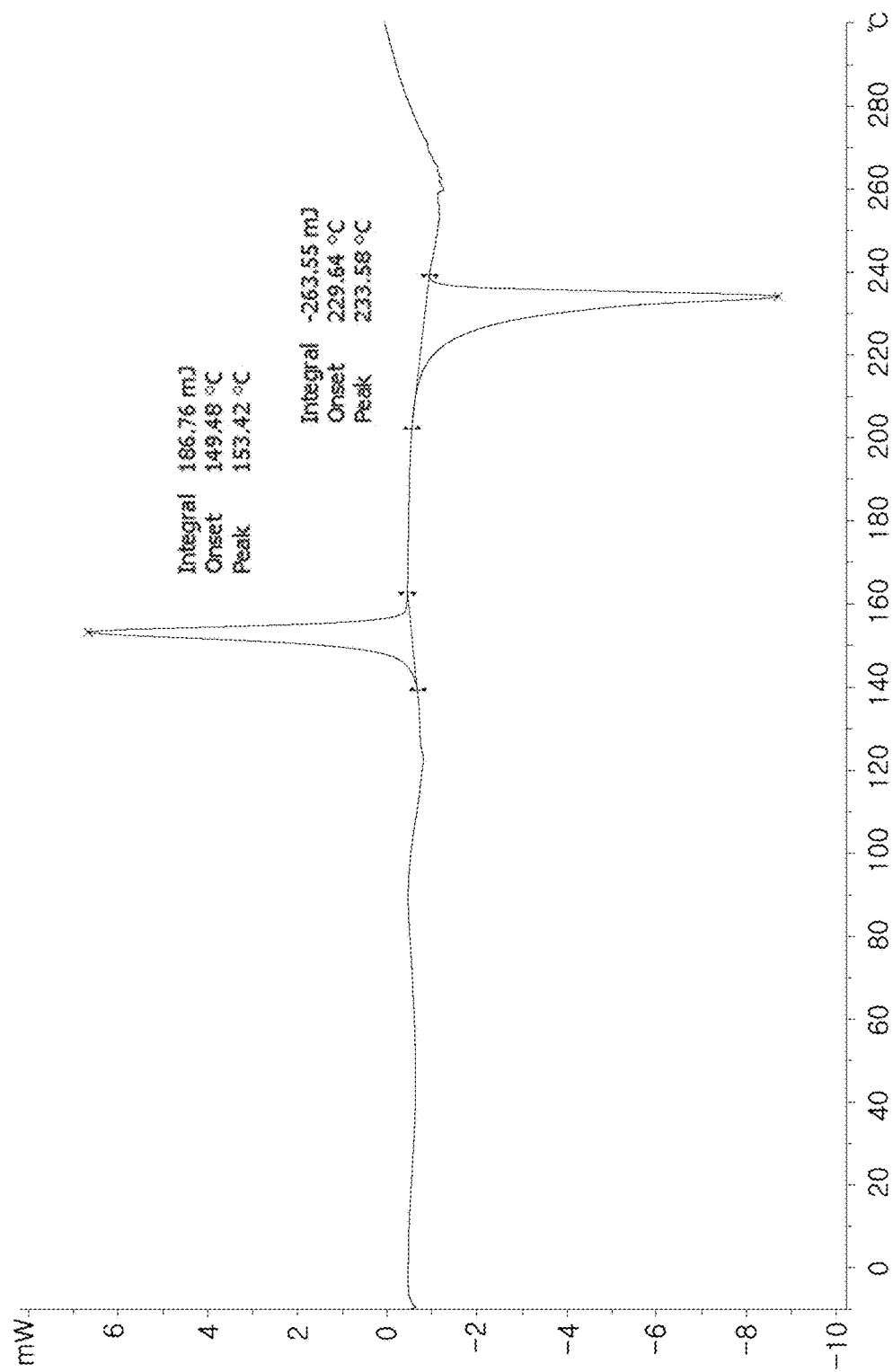
Figure 4:
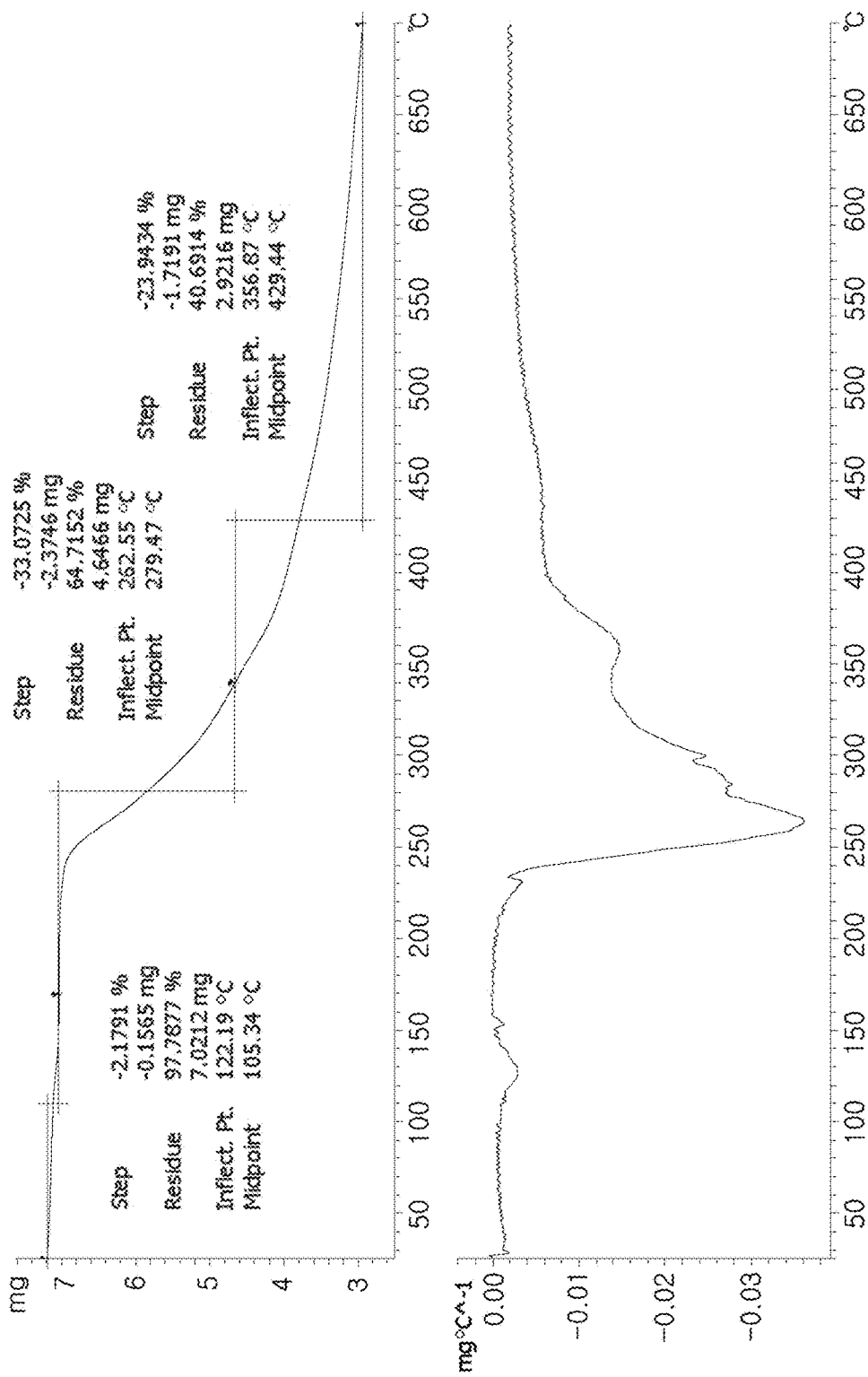

And also, the XRPD spectrum, the DSC thermogram, and the TGA thermogram of the resulting product are shown in FIGS. 2 to 4, respectively. There was observed no characteristic peak showing a diffraction angle, a distance between crystal layers, and a relative intensity in the measured XRPD spectrum; and therefore the obtained product was an amorphous compound. And also, the obtained product showed the DSC pattern exhibiting the exothermic peak at the temperature ranging from about 148° C. to about 158° C. and the endothermic peak at the temperature ranging from about 229° C. to about 239° C. (FIG. 3); and the TGA pattern exhibiting the characteristic weight loss at the temperature ranging from about 100° C. to about 110° C. and at the temperature ranging from about 274° C. to about 284° C. (FIG. 4).

Figure 5:
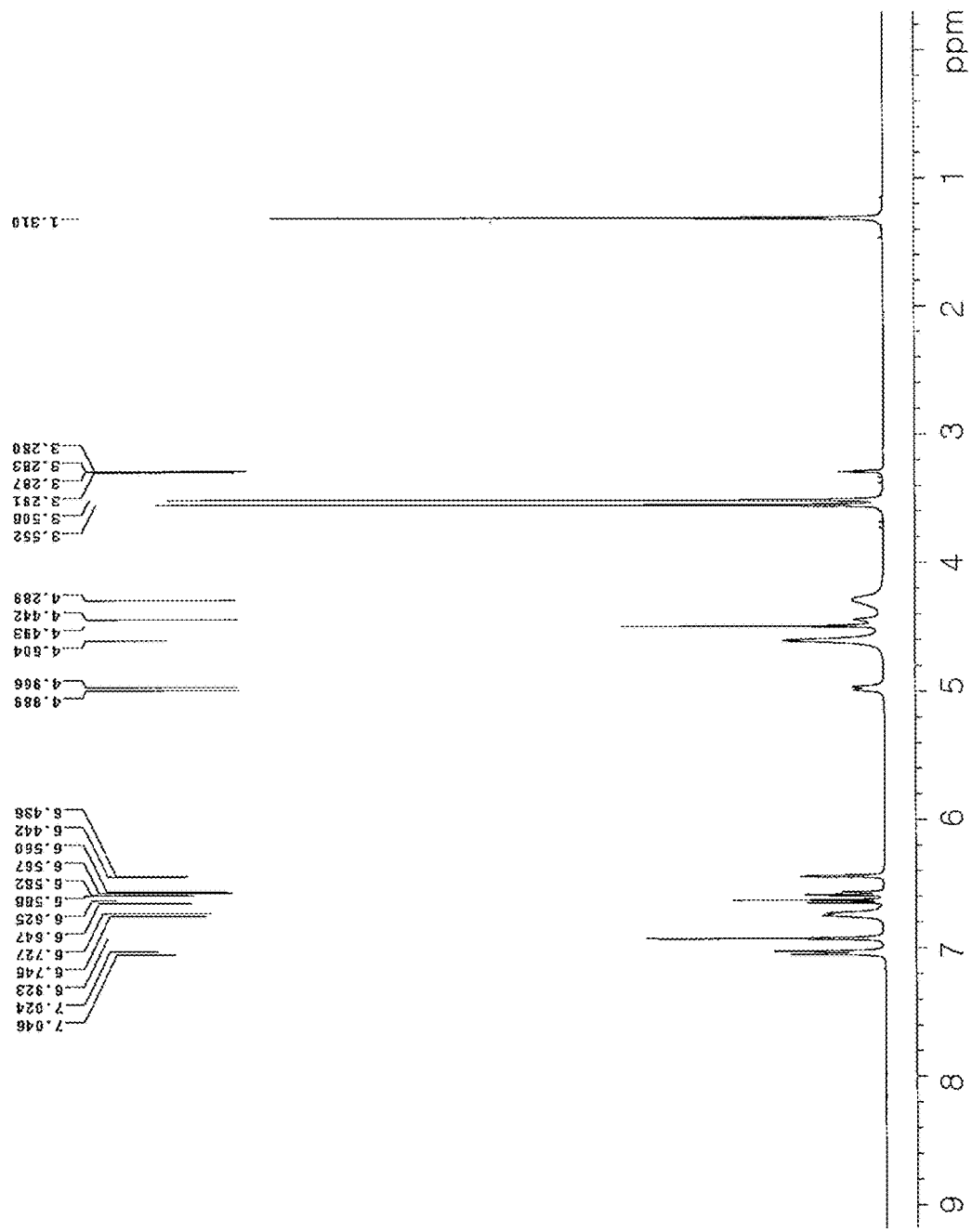
FIGS. 5 to 8 show the $^1$H-NMR spectrum (FIG. 5), the XRPD spectrum (FIG. 6), the DSC thermogram (FIG. 7), and the TGA thermogram (FIG. 8) of the crystalline form A of the compound of Formula 1 prepared according to the present invention, respectively.

Example 1: Purification of the Compound of Formula 1 Through Recrystallization and Characterization Thereof The compound of Formula 1 obtained in Preparation Example (5.00 g) was dissolved in methanol (50 mL) under reflux. The resulting solution was distilled until the solid is formed, cooled to room temperature, and then filtered under reduced pressure. The obtained solid was dried in vacuo at 50° C. for 18 hours to give 3.53 g of the compound of Formula 1 (Yield: 70.60%). The melting point, the purity (the contents of the compound of Formula 1 (as an anhydrous form) in the product), the water contents, and the $^1$H-NMR spectrum (FIG. 5) of the resulting product are as follows:

Melting point: 227-231° C.

Purity: 99.43 wt/wt %

Water contents: 0.16 wt/wt %

$^1$H-NMR (400 MHz, CD$_3$OD) δ (ppm): 1.310 (s, 3H), 3.508 (s, 3H), 3.552 (s, 3H), 4.289 (m, 2H), 4.442-4.493 (d, 2H), 4.966-4.989 (d, 1H), 6.436-6.442 (d, 1H), 6.560-6.588 (m, 1H), 6.625-6.647 (d, 1H), 6.727-6.746 (d, 2H), 6.923 (s, 2H), 7.024-7.046 (d, 2H).

Figure 6:
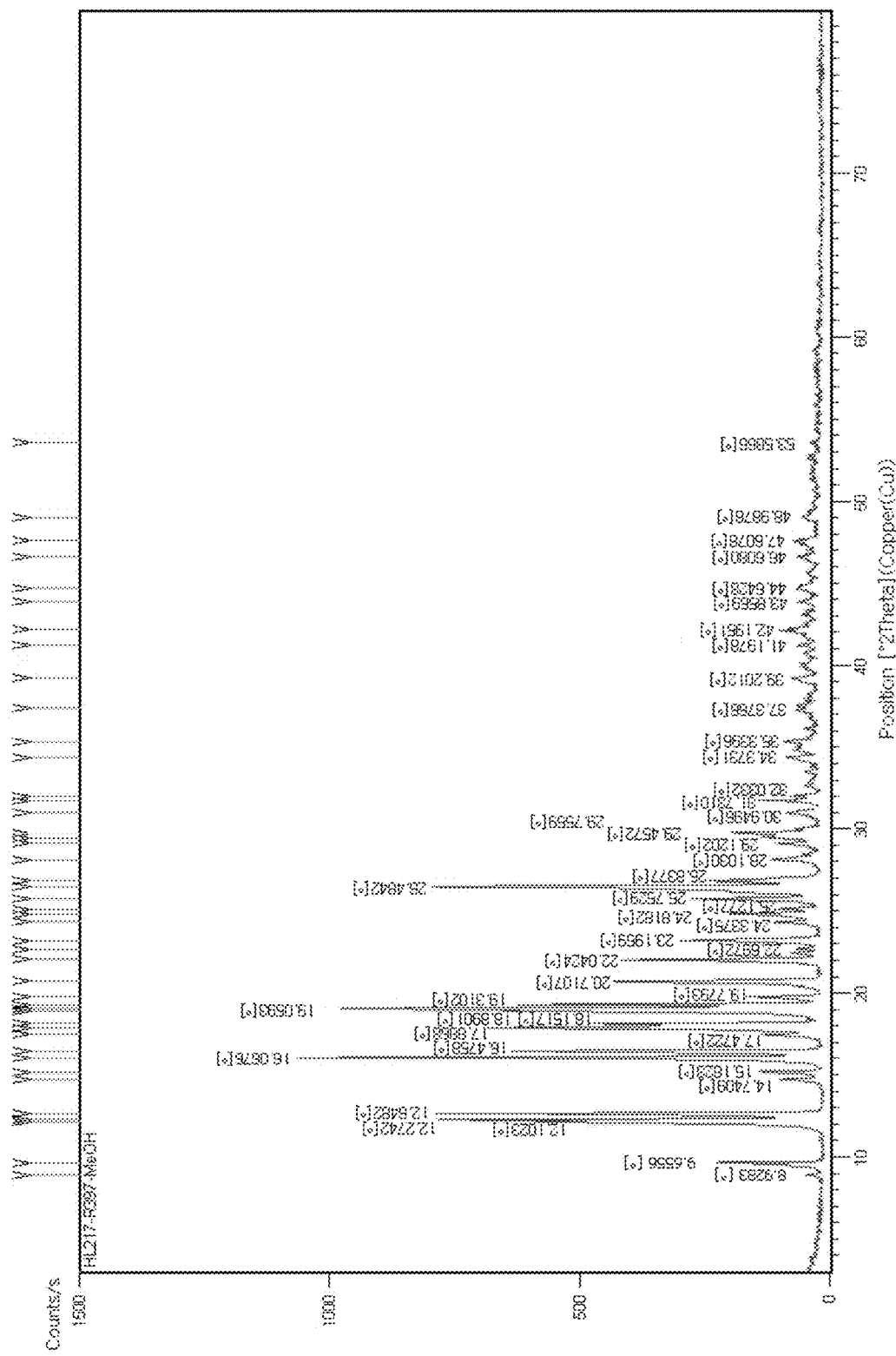

And also, the XRPD spectrum, the DSC thermogram, and the TGA thermogram of the resulting product are shown in FIGS. 6 to 8, respectively. The diffraction angles (°2θ), the distances between crystal layers (d), and the relative intensities (the relative intensity of each peak (I) with respect to the intensity of the largest peak ($I_0$), $I/I_0$) in the measured XRPD spectrum are shown in Table 1 below.

TABLE 1

| °2θ(±0.2°2θ) | d | I/I$_0$ |
|---|---|---|
| 8.93 | 9.90 | 3.33 |
| 9.66 | 9.16 | 20.67 |
| 12.10 | 7.31 | 49.77 |
| 12.27 | 7.21 | 76.85 |
| 12.65 | 7.00 | 73.83 |
| 14.74 | 6.01 | 8.38 |
| 15.18 | 5.84 | 11.98 |
| 16.07 | 5.52 | 100.00 |
| 16.48 | 5.38 | 59.88 |
| 17.47 | 5.08 | 11.19 |
| 17.89 | 4.96 | 63.09 |
| 18.15 | 4.89 | 42.97 |
| 18.89 | 4.70 | 54.02 |
| 19.06 | 4.66 | 93.08 |
| 19.31 | 4.60 | 57.62 |
| 19.78 | 4.49 | 14.29 |
| 20.71 | 4.29 | 39.98 |
| 22.04 | 4.03 | 37.17 |
| 22.70 | 3.92 | 4.45 |
| 23.20 | 3.83 | 26.85 |
| 24.34 | 3.66 | 8.70 |
| 24.82 | 3.59 | 17.66 |
| 25.13 | 3.54 | 8.17 |
| 25.75 | 3.46 | 24.44 |
| 26.48 | 3.37 | 73.77 |
| 26.84 | 3.32 | 21.40 |
| 28.10 | 3.18 | 8.73 |
| 29.12 | 3.07 | 7.73 |
| 29.46 | 3.03 | 9.35 |
| 29.76 | 3.00 | 14.71 |
| 30.95 | 2.89 | 6.06 |
| 31.73 | 2.82 | 9.11 |
| 32.03 | 2.79 | 4.99 |
| 34.37 | 2.61 | 5.17 |
| 35.34 | 2.53 | 5.97 |
| 37.38 | 2.41 | 2.57 |
| 39.20 | 2.30 | 4.71 |
| 41.20 | 2.19 | 3.27 |
| 42.20 | 2.14 | 5.29 |
| 43.86 | 2.06 | 2.58 |
| 44.64 | 2.03 | 3.34 |
| 46.61 | 1.95 | 3.01 |
| 47.61 | 1.91 | 3.53 |
| 48.99 | 1.86 | 2.54 |
| 53.59 | 1.71 | 1.17 |

Since the crystalline pattern exhibiting the characteristic peaks was confirmed from the results of Table 1, the product was a crystalline form. The crystalline form is referred to as 'a crystalline form A of the compound of Formula 1'.

Examples 2 to 8

The compound of Formula 1 was purified in accordance with the same procedures as in Example 1, except for using the different solvents according to the conditions shown in Table 2 below. The yields and the purities (the contents of the compound of Formula 1 (as an anhydrous form) in the product) are shown in Table 2. And also, since all the products showed substantially the same XRPD spectra as the XRPD spectrum shown in FIG. 6, all of the obtained products were the crystalline form A.

TABLE 2

| | Amorphous compound of Formula 1 | Solvent | Yield | Purity (wt/wt %) |
|---|---|---|---|---|
| Example 2 | 5.00 g | Ethanol 130 mL | 3.89 g (77.80%) | 99.45 |
| Example 3 | 2.00 g | Isopropanol 300 mL | 1.60 g (80.00%) | 99.40 |

TABLE 2-continued

|  | Amorphous compound of Formula 1 | Solvent | Yield | Purity (wt/wt %) |
|---|---|---|---|---|
| Example 4 | 5.00 g | Acetone 50 mL | 2.39 g (47.80%) | 99.48 |
| Example 5 | 5.00 g | Acetonitrile 100 mL | 4.10 g (82.00%) | 99.44 |
| Example 6 | 5.00 g | Dichloromethane 50 mL | 3.89 g (77.80%) | 99.45 |
| Example 7 | 5.00 g | Ethyl acetate 300 mL | 3.92 g (78.40%) | 99.50 |
| Example 8 | 5.00 g | Methyl ethyl ketone 75 mL | 2.64 g (52.80%) | 99.40 |

Example 9: Purification of the Compound of Formula 1 Using Solvent/Antisolvent and Characterization Thereof The compound of Formula 1 obtained in Preparation Example (5.00 g) was dissolved in methanol (50 mL) under reflux. Purified water (30 mL) was added to the resulting solution. The mixture was cooled to room temperature and then filtered under reduced pressure. The obtained solid was dried in vacuo at 50° C. for 18 hours to give 4.42 g of the compound of Formula 1 (Yield: 88.40%). The purity (the contents of the compound of Formula 1 (as an anhydrous form) in the product) was 99.61 wt/wt %. And also, since the product showed substantially the same XRPD spectrum as the XRPD spectrum shown in FIG. 6, the product was the crystalline form A.

Examples 10 to 18

The compound of Formula 1 was purified in accordance with the same procedures as in Example 9, except for using the different solvents/antisolvents according to the conditions shown in Table 3 below. The yields and the purities (the contents of the compound of Formula 1 (as an anhydrous form) in the product) are shown in Table 3. And also, since all the products showed substantially the same XRPD spectra as the XRPD spectrum shown in FIG. 6, all of the obtained products were the crystalline form A.

Example 19: Purification of the Compound of Formula 1 Through Crystallization by pH Control and Characterization Thereof The compound of Formula 1 obtained in Preparation Example (3.00 g) was added to purified water; and then dissolved therein by controlling to pH 1.0 with a 1N hydrochloric acid solution. The pH of the resulting solution was adjusted to pH 7.0 with a 1N sodium hydroxide solution so as to form a solid. The mixture was filtered under reduced pressure. The obtained solid was dried in vacuo at 50° C. for 18 hours to give 2.81 g of the compound of Formula 1 (Yield: 93.67%). The purity (the contents of the compound of Formula 1 (as an anhydrous form) in the product) was 99.55 wt/wt %. And also, since the product showed substantially the same XRPD spectrum as the XRPD spectrum shown in FIG. 6, the product was the crystalline form A.

Example 20: Purification of the Compound of Formula 1 Using Solvent/Antisolvent and Characterization Thereof The compound of Formula 1 obtained in Preparation Example (3.00 g) was dissolved in dichloromethane (30 mL). The resulting solution was portion wise added to hexane (300 mL) and then filtered under reduced pressure. The obtained solid was dried in vacuo at 50° C. for 18 hours to give 2.93 g of the compound of Formula 1 (Yield: 97.67%). The purity (the contents of the compound of Formula 1 (as an anhydrous form) in the product) was 99.47 wt/wt %. And also, since the product showed substantially the same XRPD spectrum as the XRPD spectrum shown in FIG. 6, the product was the crystalline form A.

Examples 21 to 24

The compound of Formula 1 was purified in accordance with the same procedures as in Example 20, except for using the different solvents/antisolvents according to the conditions shown in Table 4 below. The yields and the purities (the contents of the anhydrous compound of Formula 1 in the product) are shown in Table 4. And also, since all the products showed substantially the same XRPD spectra as the XRPD spectrum shown in FIG. 6, all of the obtained products were the crystalline form A.

TABLE 3

|  | Amorphous compound of Formula 1 | Solvent | Antisolvent | Yield | Purity (wt/wt %) |
|---|---|---|---|---|---|
| Example 10 | 5.00 g | Dimethylformamide 20 mL | Purified water 15 mL | 4.49 g (89.80%) | 99.54 |
| Example 11 | 5.00 g | Dimethyl sulfoxide 20 mL | Purified water 15 mL | 4.82 g (96.40%) | 99.59 |
| Example 12 | 5.00 g | N-methyl-2-pyrrolidone 6 mL | Purified water 60 mL | 2.80 g (93.33%) | 99.53 |
| Example 13 | 5.00 g | Dichloromethane 50 mL | Hexane 50 mL | 4.50 g (90.00%) | 99.40 |
| Example 14 | 5.00 g | Ethyl acetate 150 mL | Hexane 75 mL | 3.90 g (78.00%) | 99.47 |
| Example 15 | 5.00 g | Tetrahydrofuran 40 mL | Heptane 40 mL | 4.26 g (85.20%) | 99.39 |
| Example 16 | 5.00 g | Ethyl acetate 150 mL | Isopropyl ether 100 mL | 3.36 g (67.20%) | 99.47 |
| Example 17 | 5.00 g | Acetone 50 mL | Di-n-butyl ether 100 mL | 1.51 g (30.20%) | 99.40 |
| Example 18 | 5.00 g | Acetonitrile 100 mL | Toluene 100 mL | 2.88 g (57.60%) | 99.41 |

TABLE 4

| | Amorphous compound of Formula 1 | Solvent | Antisolvent | Yield | Purity (wt/wt %) |
|---|---|---|---|---|---|
| Example 21 | 5.00 g | Dichloromethane 30 mL | Cyclohexane 300 mL | 2.91 g (97.00%) | 99.53 |
| Example 22 | 5.00 g | Dichloromethane 30 mL | Isopropyl ether 300 mL | 2.86 g (95.33%) | 99.52 |
| Example 23 | 5.00 g | Acetone 30 mL | Diethyl ether 300 mL | 2.00 g (66.67%) | 99.42 |
| Example 24 | 3.00 g | Tetrahydrofuran 30 mL | Hexane 300 mL | 2.899 g (96.33%) | 99.46 |

Experimental Example 1: Accelerated Stability Test

The crystalline form A of the compound of Formula 1 obtained in Example 1 and the amorphous form of the compound of Formula 1 obtained in Preparation Example were stored at the accelerated condition (40° C., 75% RH) for 2 weeks, so as to evaluate the stabilities thereof. The results thereof are shown in Tables 5 and 6 below.

TABLE 5

Accelerated stability test of the crystalline form A of the compound of Formula 1

| Item | Criteria | Initial | 1 day | 2 days | 1 week | 2 weeks |
|---|---|---|---|---|---|---|
| Appearance | White or pale yellow crystalline powder | White crystalline powder | White crystalline powder | White crystalline powder | White crystalline powder | White crystalline powder |
| Water contents | 0.50% or less | 0.16% | 0.18% | 0.18% | 0.17% | 0.18% |
| Degradation products | Des-Cl*: 0.10% or less | 0.002% | 0.002% | 0.002% | 0.002% | 0.003% |
| | Unknown degradation products: 0.10% or less | 0.016% | 0.017% | 0.014% | 0.015% | 0.014% |
| | Total degradation products: 0.50% or less | 0.031% | 0.041% | 0.041% | 0.034% | 0.030% |
| Enantiomer | 0.50% or less | Not detected | Not Test | Not Test | Not Test | Not detected |
| Purity | 98.5-101.0% (as an anhydrous form) | 99.43% | Not Test | Not Test | Not Test | 99.34% |
| XRPD | | Crystalline form A | Not Test | Not Test | Not Test | Crystalline form A |

*Des-Cl: (2R,3R,4S)-6-amino-4-[N-phenyl-N-(1H-imidazol-2-ylmethyl)amino]-3-hydroxy-2-methyl-2-dimethoxymethyl-3,4-dihydro-2H-1-benzopyran

TABLE 6

Accelerated stability test of the amorphous form of the compound of Formula 1

| Item | Criteria | Initial | 1 day | 2 days | 1 week | 2 weeks |
|---|---|---|---|---|---|---|
| Appearance | White or pale yellow crystalline powder | Almost white powder | Almost white powder | Almost white powder | Almost white powder | Almost white powder |
| Water contents | 0.50% or less | 1.05% | 2.30% | 2.64% | 2.52% | 2.60% |
| Degradation products | Des-Cl*: 0.10% or less | 0.003% | 0.002% | 0.002% | 0.002% | 0.003% |
| | Unknown degradation products: 0.10% or less | 0.022% | 0.023% | 0.020% | 0.024% | 0.023% |
| | Total degradation products: 0.50% or less | 0.047% | 0.047% | 0.060% | 0.074% | 0.075% |
| Enantiomer | 0.50% or less | Not detected | Not Test | Not Test | Not Test | Not detected |
| Purity | 98.5-101.0% (as an anhydrous form) | 96.96% | Not Test | Not Test | Not Test | 96.72% |

TABLE 6-continued

Accelerated stability test of the amorphous form of the compound of Formula 1

| Item | Criteria | Initial | 1 day | 2 days | 1 week | 2 weeks |
|------|----------|---------|-------|--------|--------|---------|
| XRPD | | Amorphous form | Not Test | Not Test | Not Test | Not Test |

*Des-Cl: (2R,3R,4S)-6-amino-4-[N-phenyl-N-(1H-imidazol-2-ylmethyl)amino]-3-hydroxy-2-methyl-2-dimethoxymethyl-3,4-dihydro-2H-1-benzopyran As shown in Table 5 above, the crystalline form A of the compound of Formula 1 was stably maintained as a white crystalline powder, without any change in the appearance, under the accelerated condition. The water contents were maintained in the amount ranging from 0.16% to 0.18%, without showing a significant increase pattern; and also the contents of degradation products were maintained in the amount ranging from 0.030% to 0.041%, without showing a significant increase pattern. In addition, no enantiomer was detected during the test period. The purities ranging from 99.43% to 99.34% were within the suitable criteria thereof (i.e., from 98.5% to 101.0%) and only a decrease in the level of experimental error was observed. In the XRPD analyses, the same crystalline form A was maintained.

However, as shown in Table 6 above, the amorphous form of the compound of Formula 1 showed higher initial water contents (i.e., 1.05%) than the crystalline form; and the water contents increased up to 2.64% according to the storing time, exhibiting very high hygroscopicity. Although the initial values in the appearance, the contents of degradation products, and any enantiomer were maintained, the initial purity as an anhydrous form (96.96%) was not within the criteria, which was not changed according to the storing time. Therefore, it can be seen that the amorphous form of the compound of Formula 1 shows very high hygroscopicity under the accelerated condition for 2 weeks.

Experimental Example 2: Thermal Stability Test

The crystalline form A of the compound of Formula 1 obtained in Example 1 and the amorphous form of the compound of Formula 1 obtained in Preparation Example were stored at the heat-condition (100° C.) for 2 weeks, so as to evaluate the stabilities thereof. The results thereof are shown in Tables 7 and 8 below.

TABLE 7

Thermal stability test of the crystalline form A of the compound of Formula 1

| Item | Criteria | Initial | 1 day | 2 days | 1 week | 2 weeks |
|------|----------|---------|-------|--------|--------|---------|
| Appearance | White or pale yellow crystalline powder | White crystalline powder | White crystalline powder | White crystalline powder | Pale yellow crystalline powder | Pale yellow crystalline powder |
| Water contents | 0.50% or less | 0.16% | Not Test | Not Test | Not Test | 0.11% |
| Degradation products | Des-Cl*: 0.10% or less | 0.002% | 0.002% | 0.002% | 0.002% | 0.013% |
| | Unknown degradation products: 0.10% or less | 0.016% | 0.013% | 0.010% | 0.014% | 0.013% |
| | Total degradation products: 0.50% or less | 0.031% | 0.033% | 0.032% | 0.041% | 0.055% |
| Enantiomer | 0.50% or less | Not detected | Not Test | Not Test | Not Test | Not detected |
| Purity | 98.5-101.0% (as an anhydrous form) | 99.43% | Not Test | Not Test | Not Test | 99.25% |
| XRPD | | Crystalline form A | Not Test | Not Test | Not Test | Crystalline form A |

*Des-Cl: (2R,3R,4S)-6-amino-4-[N-phenyl-N-(1H-imidazol-2-ylmethyl)amino]-3-hydroxy-2-methyl-2-dimethoxymethyl-3,4-dihydro-2H-1-benzopyran

TABLE 8

Thermal stability test of the amorphous form of the compound of Formula 1

| Item | Criteria | Initial | 1 day | 2 days | 1 week | 2 weeks |
|------|----------|---------|-------|--------|--------|---------|
| Appearance | White or pale yellow crystalline powder | Almost white powder | Brown powder | Brown powder | Brown powder | Brown powder |

TABLE 8-continued

Thermal stability test of the amorphous form of the compound of Formula 1

| Item | Criteria | Initial | 1 day | 2 days | 1 week | 2 weeks |
|---|---|---|---|---|---|---|
| Water contents | 0.50% or less | 1.05% | Not Test | Not Test | Not Test | 0.34% |
| Degradation products | Des-Cl*: 0.10% or less | 0.003% | 0.004% | 0.004% | 0.011% | 0.017% |
|  | Unknown degradation products: 0.10% or less | 0.022% | 0.072% | 0.083% | 0.247% | 0.497% |
|  | Total degradation products: 0.50% or less | 0.047% | 0.373% | 0.362% | 0.938% | 1.811% |
| Enantiomer | 0.50% or less | Not detected | Not Test | Not Test | Not Test | Not detected |
| Purity | 98.5-101.0% (as an anhydrous form) | 96.96% | Not Test | Not Test | Not Test | 92.34% |
| XRPD |  | Amorphous form | Not Test | Not Test | Not Test | Not Test |

*Des-Cl: (2R,3R,4S)-6-amino-4-[N-phenyl-N-(1H-imidazol-2-ylmethyl)amino]-3-hydroxy-2-methyl-2-dimethoxymethyl-3,4-dihydro-2H-1-benzopyran As shown in Table 7 above, the appearance of the crystalline form A of the compound of Formula 1 was changed to pale yellow color from the first week, under the heat-condition (100° C.). The water contents were maintained in the amount ranging from 0.11% to 0.16%, without showing a significant increase pattern; and also the contents of degradation products were maintained in the amount ranging from 0.031% to 0.055%, without showing a significant increase pattern. In addition, no enantiomer was detected during the test period. The purities ranging from 99.43% to 99.25% were within the suitable criteria thereof (i.e., from 98.5% to 101.0%) and only a decrease in the level of experimental error was observed. In the XRPD analyses, the same crystalline form A was maintained.

However, as shown in Table 8 above, the amorphous form of the compound of Formula 1 showed higher initial water contents (i.e., 1.05%) than the crystalline form; and the water contents decreased to 0.34% according to the storing time. The appearance was also changed to brown color from the first day and thus unsuitable for the criteria. The contents of degradation products were increased from initial 0.047% up to 1.811%, while no enantiomer was detected during the test period. The initial purity as an anhydrous form (96.96%) was not within the criteria; and was decreased to 92.34% and thus unsuitable for the criteria. Therefore, it can be seen that the amorphous form of the compound of Formula 1 shows remarkably decreased properties, especially in the appearance, the contents in degradation products, and the purity, under the heat-condition for 2 weeks.

Experimental Example 3: Stability Test on Humidity

The crystalline form A of the compound of Formula 1 obtained in Example 1 and the amorphous form of the compound of Formula 1 obtained in Preparation Example were stored at the humid condition (25° C., 98% RH) for 2 weeks, so as to evaluate the stabilities thereof. The results thereof are shown in Tables 9 and 10 below.

TABLE 9

Stability test on humidity of the crystalline form A of the compound of Formula 1

| Item | Criteria | Initial | 1 day | 2 days | 1 week | 2 weeks |
|---|---|---|---|---|---|---|
| Appearance | White or pale yellow crystalline powder | White crystalline powder | White crystalline powder | White crystalline powder | Pale yellow crystalline powder | Pale yellow crystalline powder |
| Water contents | 0.50% or less | 0.16% | 0.21% | 0.24% | 0.29% | 0.27% |
| Degradation products | Des-Cl*: 0.10% or less | 0.002% | 0.002% | 0.003% | 0.002% | 0.004% |
|  | Unknown degradation products: 0.10% or less | 0.016% | 0.016% | 0.015% | 0.016% | 0.013% |
|  | Total degradation products: 0.50% or less | 0.031% | 0.036% | 0.030% | 0.030% | 0.029% |
| Enantiomer | 0.50% or less | Not detected | Not Test | Not Test | Not Test | Not detected |

TABLE 9-continued

Stability test on humidity of the crystalline form A of the compound of Formula 1

| Item | Criteria | Initial | 1 day | 2 days | 1 week | 2 weeks |
|---|---|---|---|---|---|---|
| Purity | 98.5-101.0% (as an anhydrous form) | 99.43% | Not Test | Not Test | Not Test | 99.32% |
| XRPD | | Crystalline form A | Not Test | Not Test | Not Test | Crystalline form A |

*Des-Cl: (2R,3R,4S)-6-amino-4-[N-phenyl-N-(1H-imidazol-2-ylmethyl)amino]-3-hydroxy-2-methyl-2-dimethoxymethyl-3,4-dihydro-2H-1-benzopyran

TABLE 10

Stability test on humidity of the amorphous form of the compound of Formula 1

| Item | Criteria | Initial | 1 day | 2 days | 1 week | 2 weeks |
|---|---|---|---|---|---|---|
| Appearance | White or pale yellow crystalline powder | Almost white powder | Almost white powder | Almost white powder | Almost white powder | Almost white powder |
| Water contents | 0.50% or less | 1.05% | 3.20% | 3.60% | 3.90% | 3.58% |
| Degradation products | Des-Cl*: 0.10% or less | 0.003% | 0.002% | 0.002% | 0.002% | 0.002% |
| | Unknown degradation products: 0.10% or less | 0.022% | 0.020% | 0.020% | 0.025% | 0.025% |
| | Total degradation products: 0.50% or less | 0.047% | 0.047% | 0.062% | 0.090% | 0.083% |
| Enantiomer | 0.50% or less | Not detected | Not Test | Not Test | Not Test | Not detected |
| Purity | 98.5-101.0% (as an anhydrous form) | 96.96% | Not Test | Not Test | Not Test | 96.55% |
| XRPD | | Amorphous form | Not Test | Not Test | Not Test | Not Test |

*Des-Cl: (2R,3R,4S)-6-amino-4-[N-phenyl-N-(1H-imidazol-2-ylmethyl)amino]-3-hydroxy-2-methyl-2-dimethoxymethyl-3,4-dihydro-2H-1-benzopyran As shown in Table 9 above, the crystalline form A of the compound of Formula 1 was stably maintained as a white crystalline powder, without any change in the appearance, under the humid condition (25° C., 98% RH). The water contents were slightly increased to the amount ranging from 0.16% to 0.29%, without showing a significant increase pattern; and also the contents of degradation products were maintained in the amount ranging from 0.029% to 0.036%, without showing a significant increase pattern. In addition, no enantiomer was detected during the test period. The purities ranging from 99.43% to 99.32% were within the suitable criteria thereof (i.e., from 98.5% to 101.0%) and only a decrease in the level of experimental error was observed. In the XRPD analyses, the same crystalline form A was maintained.

However, as shown in Table 10 above, the amorphous form of the compound of Formula 1 showed higher initial water contents (i.e., 1.05%) than the crystalline form; and the water contents increased up to 3.90% according to the storing time, exhibiting very high hygroscopicity. Although the appearance of almost white powder was not changed, the contents of degradation products were increased from initial 0.047% up to 0.090%. Although no enantiomer was detected during the test period, the initial purity as an anhydrous form (96.96%) was not within the criteria, which was not changed according to the storing time. Therefore, it can be seen that the amorphous form of the compound of Formula 1 shows hygroscopicity under the humid condition for 2 weeks.

The invention claimed is:

1. A crystalline form of the compound of Formula 1:

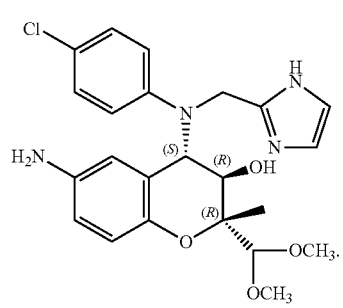

<Formula 1>

2. The crystalline form according to claim 1, wherein the crystalline form of the compound of Formula 1 is a crystalline form A having an XRPD pattern with peaks at 12.27, 12.65, 16.07, 19.06 and 26.48°2θ±0.2°2θ.

3. The crystalline form according to claim 1, wherein the crystalline form of the compound of Formula 1 is a crystalline form A having an XRPD pattern with peaks at 12.27, 12.65, 16.07, 16.48, 17.89, 18.89, 19.06, 19.31 and 26.48°2θ±0.2°2θ.

4. The crystalline form according to claim 1, wherein the crystalline form of the compound of Formula 1 is a crystalline form A having a differential scanning calorimetry (DSC) thermogram showing an endothermic peak at between 240° C. and 250° C.

5. The crystalline form according to claim 1, wherein the crystalline form of the compound of Formula 1 is a crystalline form A having a thermogravimetric analysis (TGA) thermogram showing a weight loss at between 300° C. and 310° C.

6. A process for purifying a compound of Formula 1, comprising converting a crude compound of Formula 1 to a crystalline form thereof:

<Formula 1>

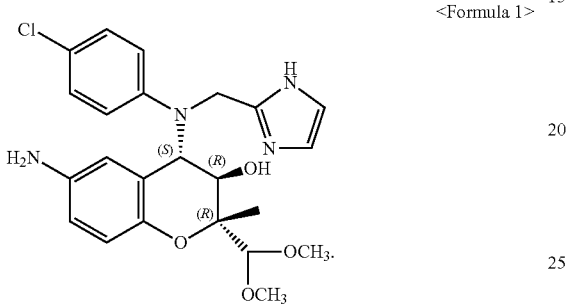

7. The process according to claim 6, wherein the crude compound of Formula 1 is in an amorphous form.

8. The process according to claim 6, wherein the crystalline form is a crystalline form A of the compound of Formula 1 having an XRPD pattern with peaks at 12.27, 12.65, 16.07, 19.06 and 26.48°2θ±0.2°2θ.

9. The process according to claim 6, wherein the crystalline form is a crystalline form A of the compound of Formula 1 having an XRPD pattern with peaks at 12.27, 12.65, 16.07, 16.48, 17.89, 18.89, 19.06, 19.31 and 26.48°2θ±0.2°2θ.

10. The process according to claim 6, wherein the crystalline form is a crystalline form A of the compound of Formula 1 having a differential scanning calorimetry (DSC) thermogram showing an endothermic peak at between 240° C. and 250° C.

11. The process according to claim 6, wherein the crystalline form is a crystalline form A of the compound of Formula 1 having a thermogravimetric analysis (TGA) thermogram showing a weight loss at between 300° C. and 310° C.

12. A process for preparing a crystalline form of the compound of Formula 1, comprising dissolving an amorphous compound of Formula 1 in an organic solvent to obtain a solution; stirring, distilling, or cooling the solution to form a solid or distilling and then cooling the solution to form a solid; and isolating the solid:

<Formula 1>

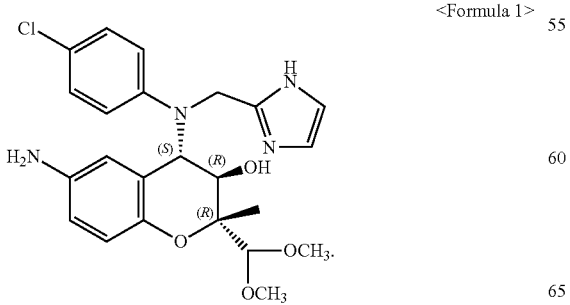

13. The process according to claim 12, wherein the organic solvent is one or more selected from the group consisting of methanol, ethanol, isopropanol, acetone, methyl ethyl ketone, acetonitrile, ethyl acetate, dichloromethane, tetrahydrofuran, dimethyl sulfoxide, dimethylformamide, and N-methyl-2-pyrrolidone.

14. A process for preparing a crystalline form of the compound of Formula 1, comprising dissolving an amorphous compound of Formula 1 in an organic solvent to obtain a solution; adding the solution to an antisolvent to form a solid or adding an antisolvent to the solution to form a solid; and isolating the solid:

<Formula 1>

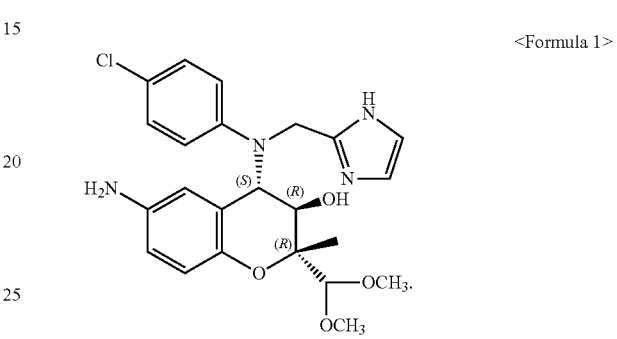

15. The process according to claim 14, wherein the organic solvent is one or more selected from the group consisting of methanol, ethanol, isopropanol, acetone, methyl ethyl ketone, acetonitrile, ethyl acetate, dichloromethane, tetrahydrofuran, dimethyl sulfoxide, dimethylformamide, and N-methyl-2-pyrrolidone.

16. The process according to claim 14, wherein the antisolvent is one or more selected from the group consisting of water, hexane, heptane, diethyl ether, isopropyl ether, di-n-butyl ether, and toluene.

17. A process for preparing a crystalline form of the compound of Formula 1, comprising dissolving an amorphous compound of Formula 1 in water by adding an acid thereto to obtain a solution; adding a base to the solution to form a solid; and isolating the solid:

<Formula 1>

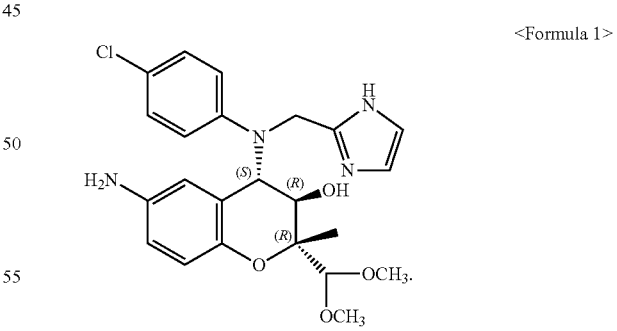

18. The process according to claim 17, wherein the acid is one or more selected from the group consisting of hydrochloric acid, acetic acid, and formic acid.

19. The process according to claim 17, wherein the base is one or more selected from the group consisting of sodium hydroxide, potassium hydroxide, sodium bicarbonate, and sodium carbonate.

20. The process according to claim 12, wherein the crystalline form of the compound of Formula 1 is a crystalline form A having an XRPD pattern with peaks at 12.27, 12.65, 16.07, 19.06 and 26.48°2θ±0.2°2θ.

21. The process according to claim 12, wherein the crystalline form is a crystalline form A having an XRPD pattern with peaks at 12.27, 12.65, 16.07, 16.48, 17.89, 18.89, 19.06, 19.31 and 26.48°2θ±0.2°2θ.

22. The process according to claim 12, wherein the crystalline form is a crystalline form A having a differential scanning calorimetry (DSC) thermogram showing an endothermic peak at between 240° C. and 250° C.

23. The process according to claim 12, wherein the crystalline form is a crystalline form A having a thermogravimetric analysis (TGA) thermogram showing a weight loss at between 300° C. and 310° C.

* * * * *